United States Patent
Miyai

(10) Patent No.: US 6,603,780 B2
(45) Date of Patent: Aug. 5, 2003

(54) LASER APPARATUS, LASER-APPLIED APPARATUS AND METHOD FOR USING SAME

(75) Inventor: Tsuyoshi Miyai, Saitama-ken (JP)

(73) Assignee: Hitachi Metals, Ltd., Tokyo (JP)

( * ) Notice: Subject to any disclaimer, the term of this patent is extended or adjusted under 35 U.S.C. 154(b) by 0 days.

(21) Appl. No.: 09/748,197

(22) Filed: Dec. 27, 2000

(65) Prior Publication Data

US 2001/0015990 A1 Aug. 23, 2001

(30) Foreign Application Priority Data

Dec. 27, 1999 (JP) .......................................... 11-368870

(51) Int. Cl.⁷ ............................................... H01S 3/102
(52) U.S. Cl. ............................................. 372/23; 372/9
(58) Field of Search ................................ 372/23, 9, 20; 385/115; 606/3

(56) References Cited

U.S. PATENT DOCUMENTS

| | | | | |
|---|---|---|---|---|
| 5,090,416 A | * | 2/1992 | Ogino et al. | 600/504 |
| 5,331,649 A | * | 7/1994 | Dacquay et al. | 372/23 |
| 5,586,132 A | * | 12/1996 | Levy | 372/23 |
| 5,811,751 A | * | 9/1998 | Leong et al. | 219/121.6 |
| 5,864,643 A | | 1/1999 | Pan | |
| 6,011,809 A | * | 1/2000 | Tosaka | 372/23 |
| 6,061,319 A | | 5/2000 | Fujiki | |
| 6,104,477 A | | 8/2000 | Yoshida et al. | |
| 6,394,788 B1 | * | 5/2002 | Early et al. | 372/23 |

FOREIGN PATENT DOCUMENTS

| | | |
|---|---|---|
| DE | 4115401 | 11/1992 |
| DE | 19806627 | 9/1999 |
| DE | 19827139 | 12/1999 |
| EP | 0917262 | 5/1999 |
| JP | 6-214162 | 8/1994 |
| JP | 9-243598 | 9/1997 |
| JP | 11-127900 | 5/1999 |
| JP | 11-183324 | 7/1999 |
| JP | 11-243997 | 9/1999 |

* cited by examiner

*Primary Examiner*—Albert W. Paladini

(57) ABSTRACT

A laser apparatus for selectively supplying a plurality of laser beams of 30 nm or more in wavelength difference to a measuring apparatus includes optical fibers through which the laser beams pass, and a switching and coupling means connected to the optical fibers for selecting at least one laser beam from a plurality of laser beams. A laser-applied apparatus includes this laser apparatus, and a fluorescent microscope, a DNA sequencer, or an examination apparatus selected from a DNA chip examination apparatus, protein examination apparatus and a DNA probe array examination apparatus.

15 Claims, 5 Drawing Sheets

LASER APPARATUS, LASER-APPLIED APPARATUS AND METHOD FOR USING SAME

FIELD OF THE INVENTION

The present invention relates to a laser apparatus, particularly to a laser apparatus emitting and receiving a plurality of laser beams of different wavelengths and its applications.

BACKGROUND OF THE INVENTION

Laser beams are widely used in various industries such as optical communications. For instance, U.S. Pat. No. 6,061,319 and Japanese Patent Laid-Open No. 11-183324 disclose laser apparatuses comprising switching means. Particularly, U.S. Pat. No. 6,061,319 discloses a fiber laser apparatus for use in optical communications comprising wavelength-selecting means having a plurality of oscillating wavelengths with wavelength difference of 100 GHz (0.8 nm) in a 1.5-$\mu$m band. Also, Japanese Patent Laid-Open No. 11-183324 discloses an optical switch for switching the ON/OFF of a plurality of laser beam sources and measuring paths. However, there is room for improvement in them in terms of reliability, operability and miniaturization.

Also known as measurement apparatuses utilizing laser beams are microscopes such as a scanning-type, confocal microscope. This scanning-type, confocal microscope is an apparatus irradiating a laser beam to an object to be measured, and observing a fluorescent beam emitted from the object. Because the scanning-type, confocal microscope can focus on a much narrower region than usual microscopes, it can selectively observe a portion having a particular thickness in a stereoscopic sample. This confocal microscope is used, for instance, in the quantitative observation of the locality of proteins in cells as basic data for genetic information. In this measurement, fluorescent labels are given to several types of proteins having different molecular structures. Because fluorescent labels absorb light beams of particular wavelengths, exciting light beams should be present in the same number as that of the fluorescent labels.

Laser beams used for exciting beams range from ultraviolet to red. The details of a scanning-type, confocal microscope using laser beams are described in Japanese Patent Laid-Open No. 6-214162. Further, Japanese Patent Laid-Open Nos. 9-243598, 11-127900 and 11-243997 disclose DNA sequencers and DNA chip examination apparatuses as laser-applied apparatuses.

In the identification of proteins using a confocal microscope according to the above conventional procedures, there have been problems as described below in the course of measurement. That is, the conventional measurement procedures require that exciting light sources be switched in the observation from a certain protein to a next protein. Specifically, after a laser beam source is disconnected from a microscope, another laser beam source of a different wavelength is connected to the microscope. Such troublesome disconnecting and connecting operations of laser beam sources and a microscope are required whenever objects to be measured are changed, posing problems that an operator may be exposed directly to laser beams. Further, because an operator frequently disconnect a connector having fiber ends exposed mechanically from the apparatus, the fiber ends are likely to be damaged, resulting in trouble and deterioration of performance. In addition, the damage of the fiber ends is difficult to find by the naked eye, leading to deterioration in reliability and reproducibility of data.

In view of such problems, laser apparatuses designed to eliminate such troublesome changing operations and to avoid dangerous operations were devised and put into practical use. This apparatus is schematically shown in FIG. 8. This apparatus comprises an optical Table 70, and three laser beam sources 72-1, 72-2, 72-3 of different wavelengths arranged as shown in FIG. 8, wherein laser beams emitted from laser beam sources 72-1, 72-2, 72-3 are guided to focusing lenses 78-1, 78-2 in a focusing system 75 by mirrors 76-1, 76-2, 76-3, and supplied to a laser-applied apparatus 19 via an optical fiber 17. Because each mirror 76-1, 76-2, 76-3 has a wavelength selectivity that reflects a laser beam of a wavelength emitted from the corresponding laser beam source 72-1, 72-2, 72-3 while permitting laser beams of other wavelengths to pass through, laser beams of different wavelengths can properly be selected without carried out the above-described switching operations. In with this constitution, a light path from a laser beam source 72 to a focusing lens 78 is the air (air-waveguide system).

However, in this conventional apparatus, optical parts such as the optical table 70 and the mirrors 76 may be elongated, deformed or displaced from their original positions due to change in the ambient temperature and heat generated from the laser beam sources 72, resulting in change in the light paths as shown by the dotted lines in FIG. 8. As a result, coupling decreases between the laser beam sources 72 and the optical fiber 17, failing to provide laser beams necessary for the laser-applied apparatus 19 such as a microscope, and thus failing to expect normal operations of the laser-applied apparatus.

In addition, because a plurality of laser beam sources 72 are mounted two-dimensionally onto the optical table 70, a rather wide optical table is needed, resulting in difficulty in disposing it in a proper narrow place. For instance, in the case of mounting three or four laser beam sources onto an optical table, an optical table as wide as up to 1 $m^2$ is needed in the conventional technologies. Further, because of the air-waveguide system, a structure for shielding the light path and its surrounding should be added to ensure safety. Thus, the conventional laser apparatus per se is large and not easy to handle.

OBJECT OF THE INVENTION

Accordingly, an object of the present invention is to solve the problems of the prior art technologies by changing a waveguide system from the air-waveguide system to an optical fiber-waveguide system.

DISCLOSURE OF THE INVENTION

The laser apparatus according to the present invention has a structure in which a laser beam emitted from each laser beam source is led to a switching and coupling means via an input optical fiber, and one of a plurality of input optical fibers is arbitrarily selected such that a desired laser beam is supplied to a laser-applied apparatus.

The switching and coupling means has a structure in which the desired one of a plurality of optical fibers can be selected, and which input optical fibers and output optical fibers are positioned with such high accuracy that loss at coupling can be suppressed as much as possible. Also, with a control circuit connected to the switching and coupling means, the ON/OFF time and sequence can be controlled according to the predetermined program, thereby providing a laser apparatus with more diversified functions and applicability. Particularly in the biomedical applications, a plurality of laser beams of 30 nm or more in wavelength difference can be switched by the switching and coupling means, thereby eliminating troublesome and dangerous operations and thus improving reliability and operability with further miniaturization.

The laser apparatus for selectively supplying a plurality of laser beams of 30 nm or more in wavelength difference to a measuring apparatus according to the present invention comprises optical fibers through which the laser beams pass, and a switching and coupling means connected to the optical fibers for selecting at least one laser beam from a plurality of laser beams. The laser beams preferably have a wavelength of 350–800 nm.

The switching and coupling means preferably has at least a function to turn off said laser beams. A plurality of switching and coupling means preferably are connected in series or in parallel.

In a preferred embodiment of the present invention, the laser apparatus for selectively supplying a plurality of laser beams of 30 nm or more in wavelength difference to a measuring apparatus comprises a plurality of laser beam sources for emitting laser beams having different wavelengths; a plurality of input optical fibers each connected to the laser beam source, through which the laser beams pass; at least one switching and coupling means having a plurality of inputs connected to the input optical fibers and at least one output for selecting at least one laser beam from a plurality of the laser beams; at least one output optical fiber connected to the output of the switching and coupling means; and a measuring apparatus connected to the output optical fiber.

In another embodiment of the present invention, the switching and coupling means comprises input terminals connected to the input optical fibers together with at least one NULL terminal not connected to the input optical fiber, the terminals being arranged in parallel at an equal interval, wherein the output optical fiber is slidable transversely relative to the parallel arrangement of the terminals, such that the output optical fiber is connected to one of the terminals.

The laser-applied apparatus according to the present invention comprises the above laser apparatus, and a fluorescent microscope.

The laser-applied apparatus preferably comprises the above laser apparatus, and a DNA sequencer. The laser-applied apparatus preferably comprises the above laser apparatus, and an examination apparatus connected to the laser apparatus. The examination apparatus is preferably a DNA chip examination apparatus, protein examination apparatus or a DNA probe array examination apparatus.

In the method for using the above laser apparatus according to the present invention, laser beams supplied from the laser apparatus are introduced into at least two types of laser-applied apparatuses.

The accurate positioning of a plurality of input optical fibers in parallel at an equal interval and the position control of output optical fibers by sliding can be achieved by applying technologies developed in the technical field of optical communications or combining them with conventional technologies.

Further, with a NULL terminal capable of keeping an OFF state added to the switching and coupling means, troubles at the time of switching can be prevented. That is, the NULL terminal can prevent unnecessary light beams from being transmitted to the laser-applied apparatus at the time of switching the optical fibers, thus extremely effective as a means for suppressing strayed laser beams. Thus, the reliability of the measured data is further improved. Also with this NULL terminal, the ON/OFF control of laser beams is easily conducted, making it possible to control the irradiation time of laser beams accurately.

BEST MODE FOR CARRYING OUT THE INVENTION

Figure 1:
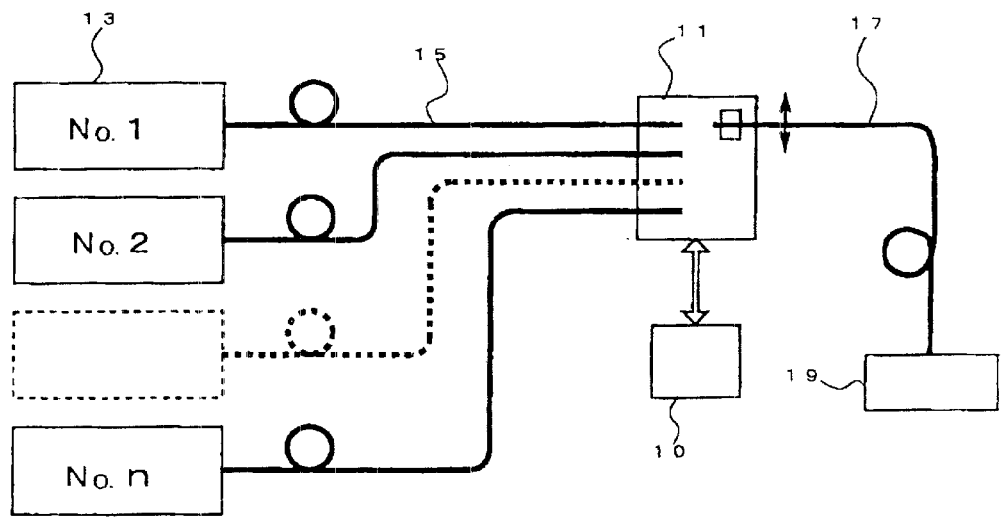
FIG. 1 is a schematic view showing the principle of the present invention.

FIG. 1 shows the principle of the present invention. In the depicted apparatus, the number of laser beam sources used is n, though it is not restrictive, and the more the laser beam sources, the more effects of the present invention can be obtained. In FIG. 1, optical fibers 15 connected to the laser beam sources 13 for guiding laser beams emitted therefrom are connected to the input side of the switching and coupling means 11 at predetermined positions and intervals. On the other hand, one optical fiber 17 is connected to the output side of the switching and coupling means 11 to select a laser beam of a desired wavelength. With respect to the positioning and fixing of the input and output optical fibers 15, 17 to the switching and coupling means 11, and the movement and position control of the optical fiber 17, the technologies of optical switching conventionally used in optical communications can be applied. The same is true of their movement mechanism and control method.

In the present invention, laser beams are guided through optical fibers, and the number of optical parts used is minimized, so that influences of the changing ambient temperature on the thermal expansion of an optical table and other optical parts can be suppressed as much as possible. Further, changes of parts with time have little influence, resulting in an apparatus with high reliability.

Though the laser beam sources 13 are disposed two-dimensionally in FIG. 1, they should not necessarily be disposed at accurate positions unlike the conventional technologies because the optical fibers are used, allowing such three-dimensional arrangements that the laser beam sources are stacked or disposed staggeringly. For the reasons described above, the positioning of optical parts and their operability are greatly improved. Further, because of three-dimensional arrangements, the laser apparatus per se can be drastically miniaturized.

For the purpose of controlling the operation of the switching and coupling means 11 and reducing the burden of operators by programming its switching order and timing, etc., a controller 10 is connected to the switching and coupling means 11. This controller 10 comprises a microcomputer that enables not only the above functions but also position control program of the optical fiber 17 on the output side, thereby being able to control the coupling of input and output in the optimum condition. With such a controller 10, the laser apparatus can meet needs of diversified measurements and high accuracy. Also, the laser apparatus is preferably provided with a means for knowing information about when the laser apparatus attached to the microscope is turned on or switched to determine the variation of a fluorescent light with time. For instance, the laser apparatus is preferably provided with an image-treating means, and a remote controller for providing a command to the switching and coupling means 11 to control the ON/OFF of the laser beams based on data supplied from the image-treating means.

Figure 2:
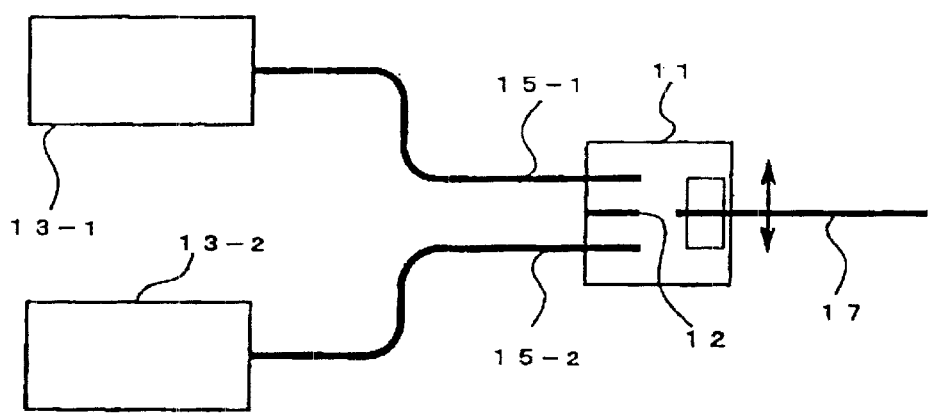
FIG. 2 is a schematic view showing a laser apparatus comprising two switchable laser beam sources according to one embodiment of the present invention.

FIG. 2 shows a laser apparatus comprising two switchable laser beam sources 13-1, 13-2 according to one embodiment of the present invention. A switching and coupling means 11 is an essential element in the present invention, and a plurality of switching and coupling means 11 may be connected in series or in parallel. With a NULL terminal 12 attached to the switching and coupling means 11, it is possible to provide a condition that no laser beam emitted from any laser beam source 13 is transmitted to the output optical fiber 17. However, the effects of the present invention can be fully obtained even when the NULL terminal 12 is omitted.

Figure 3:
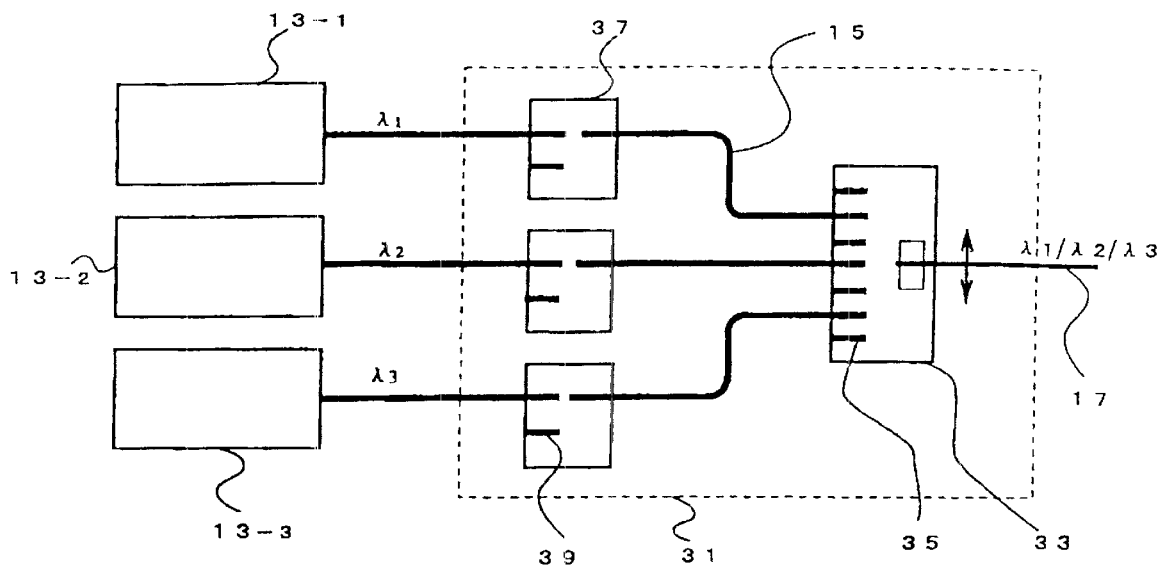
FIG. 3 is a schematic view showing a laser apparatus comprising three switchable laser beam sources according to another embodiment of the present invention.

FIG. 3 shows a laser apparatus according to another embodiment of the present invention. This laser apparatus comprises three laser beam sources 13-1, 13-2, 13-3 on the input side of a switching and coupling means 31, serving as a basic constituent for a system comprising three or more laser beam sources. As compared with the laser apparatus comprising two inputs shown in FIG. 2, the switching and coupling means 31 in the laser apparatus of FIG. 3 is different in ON/OFF operating means 37. With such multi-stage means, three laser beam sources 13-1, 13-2, 13-3 of different wavelengths $\lambda_1, \lambda_2, \lambda_3$ disposed one-dimensionally are more easily switched. When optical fibers not adjacent each other are switched, for instance when $\lambda_1$ and $\lambda_3$ are connected, the middle laser beam source 13-2 of $\lambda_2$ can be turned off by the middle ON/OFF operating means 37. Thus, such switching is achieved without connecting $\lambda_2$ to the laser-applied apparatus.

Alternatively, the switching and coupling means 33 may be modified to an integral, multi-stage means comprising an ON/OFF operating means and a switching and coupling means. Further, instead of one-dimensional arrangement of the input terminals of the switching and coupling means 33 as shown in FIG. 3, they may be arranged two-dimensionally. Incidentally, a controller for controlling the switching and coupling means 33 is not depicted in FIGS. 2 and 3, though it may naturally be connected to the switching and coupling means 33 in the present invention.

Figure 4:
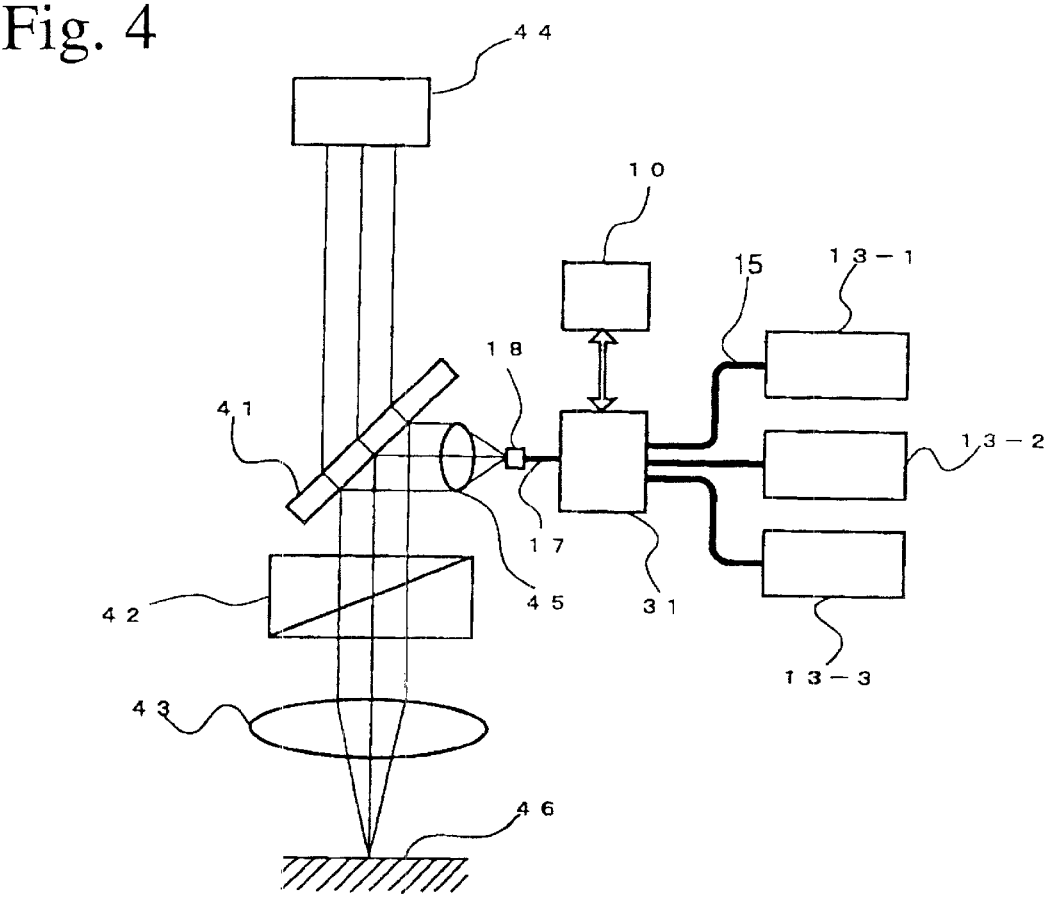
FIG. 4 is a schematic view showing a laser-applied apparatus comprising a laser apparatus coupled with a scanning-type, confocal microscope according to a further embodiment of the present invention.

FIG. 4 shows the laser apparatus of the present invention connected to a fluorescent microscope. In a preferred embodiment, a laser beam source 13-1 is a blue SHG laser beam source having a wavelength of 430 nm, a laser beam source 13-2 is an Ar laser beam source having a wavelength of 488 nm, and a laser beam source 13-3 is a green SHG laser beam source having a wavelength of 532 nm. A laser beam emitted from each laser beam source passes through an optical fiber 15 connected to a switching and coupling means 31. The output of the switching and coupling means 31 is supplied via an optical fiber 17 to a laser beam-introducing means 18 disposed on the side of a fluorescent microscope. The laser beam selected by the switching and coupling means 31 passing through a lens 45 is reflected by a dichroic mirror 41 and irradiates a sample 46 via an object lens 43. The sample 46 is labeled with a fluorescent material that simultaneously emits a reflected light and a fluorescent light having different wavelengths upon irradiated with a laser beam. These laser beams pass through substantially the same path as that of an incident light in an opposite direction, and separated by the dichroic mirror 41.

The reflected light is reflected again by the dichroic mirror 41 and returns to the laser beam-introducing means 18, while the fluorescent light passes through the dichroic mirror 41 to enter into a light detector 44 as an observed image. In this case, if it were devised to prevent the laser beam from returning to the laser beam-introducing means 18, the laser beam intensity would be further stabilized. For this purpose, it is desirable to insert a light isolator. Incidentally, the optical fiber 17 and the laser beam-introducing means 18 may be omitted by fixing the switching and coupling means 31 to the microscope.

The properties of the fluorescent materials used affect the amount of information of a sample to be measured. Accordingly, to obtain a lot of information on a sample, the sample should be labeled with plural types of fluorescent materials emitting different wavelengths. Also, different fluorescent materials have different exciting wavelengths. In this example, therefore, by labeling the sample with fluorescent materials having three different wavelengths, laser beams of 430 nm, 488 nm and 532 nm are selected as suitable wavelengths for being absorbed by the fluorescent materials. Also, in the same small region irradiated in the microscope, the irradiating laser beams can be switched at a high speed on the order of milli-second to obtain information about instantaneous dynamic characteristics and interaction of the sample.

To apply the present invention to a scanning-type, confocal microscope, a two-dimensional scanning apparatus 42 may be disposed on a light path of the microscope, and a pinhole means may be disposed between a laser beam-introducing means 18 and a light-detecting means 44. Further, an image-treating technology operable in a time division manner can be applied to obtain information from a continuous region of a sample at a high speed. Such time-divided information is expressed, for instance, by an intensity distribution of fluorescent light. Thus, it is particularly important to ensure the reliability of data that one type of laser beam is stable in intensity with time.

The present invention provides a switching and coupling means for a laser apparatus without utilizing an air-waveguide system, which is much higher in reliability as compared with the conventional air-waveguide laser apparatus. Further, because laser beams need not be transmitted through the air as the condition for using a microscope except when the laser apparatus is installed, extremely safe operation environment can be achieved. Further, because the laser beams are guided through the optical fibers, the laser beam sources need not be disposed at predetermined positions, high freedom in positioning can be achieved in a relatively narrow operation space, resulting in drastic improvement in operability such as the preparation of samples, etc. Substantially the same effects can be obtained even if part of the constitution shown in FIG. 4 is modified. Also, the matching of fluorescent materials used and the laser beam sources is important, and the number of laser beam sources may be changed depending on information to be sought without deviating from the scope of the present invention.

Figure 5:
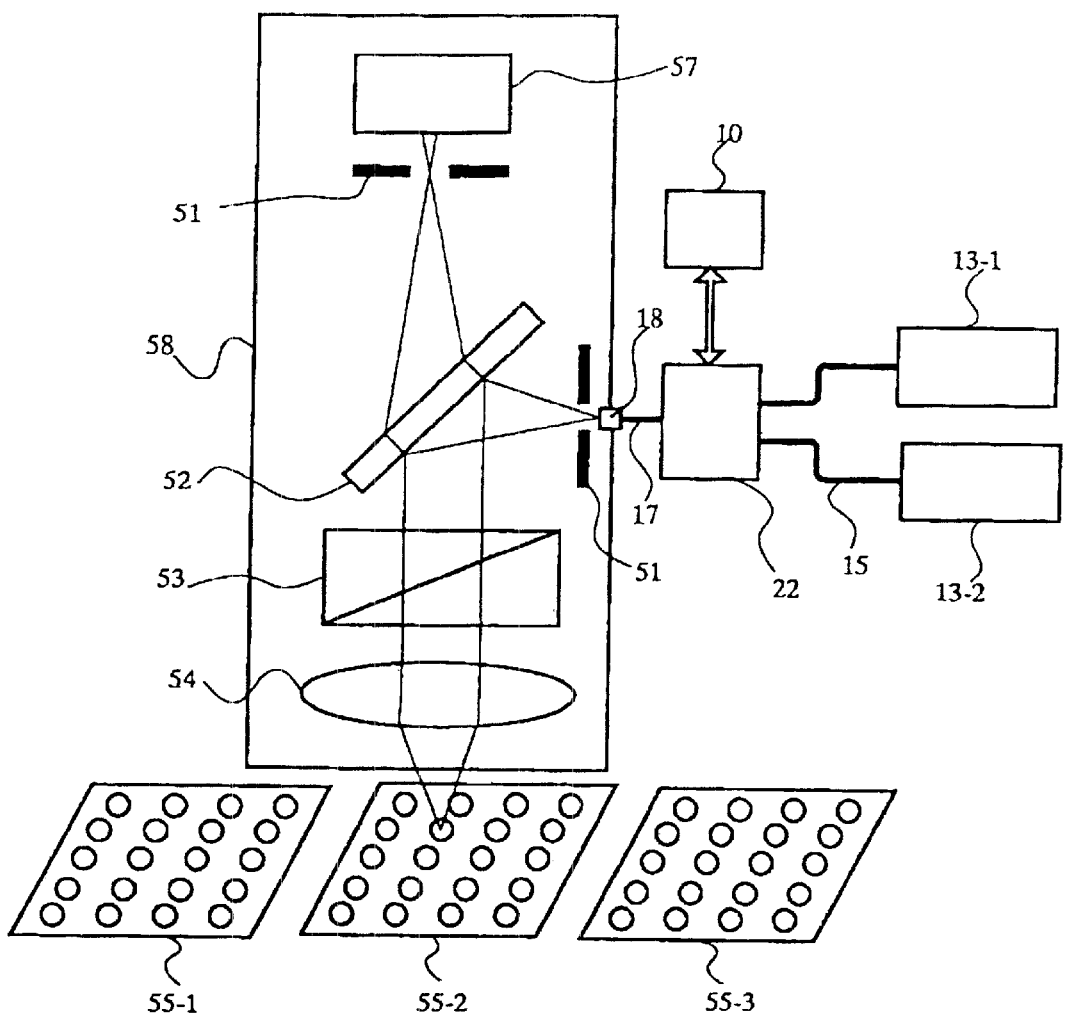
FIG. 5 is a schematic view showing a laser-applied apparatus comprising a laser apparatus coupled with a DNA chip examination apparatus according to a still further embodiment of the present invention.

FIG. 5 shows the laser apparatus of the present invention for supplying output laser beams to a DNA chip examination apparatus. As two laser beam sources having different wavelengths, a small green SHG laser beam source 13-1 having a wavelength of 532 nm, and a semiconductor laser beam source 13-2 having a wavelength of 635 nm are connected to optical fibers 15, which are then connected to a DNA chip examination apparatus via a switching and coupling means 22 according to a system as shown in FIG. 2. The laser beam selected by the switching and coupling means 22 is guided to the laser beam-introducing means 18 via an optical fiber 17. The laser beam passing through the pinhole means 51 is reflected by a dichromic mirror 52, and controlled in an x-y plane by a two-dimensional scanning apparatus 53.

Objects to be examined may be protein chips. In this example of the present invention, a DNA chip used has segments of 100×100 matrices in a 1-cm² region on a glass substrate. An irradiation range of the laser beam is a circle of 10 μm or less in diameter so that information in a segment of the DNA chip 55 can fully be resolved. Each segment of the DNA chip 55 is labeled with two types of fluorescent materials, so that upon irradiated with a laser beam, it emits a reflected light and a fluorescent light simultaneously. These lights return substantially through the input light path and separated by the dichromic mirror 52. The reflected light is reflected by the dichromic mirror 52, returning to the laser beam-introducing means 18, while the fluorescent light passes through the dichromic mirror 52 and the pinhole means 51 to reach a light detector 57 where it is received as an observed image. In the present invention, to continuously treat a plurality of DNA chips 55-1 to 55-3 arranged, the above optical system and the light examination apparatus 57 may be integrated with a driving mechanism 58. Incidentally, the controller shown in FIG. 5 can conduct different controls depending on various demands.

In the DNA chip examination apparatus of the present invention, because each segment affects individual medical diagnoses, the reliability of data in EXAMPLE shown in FIG. 4 is increasingly important. The miniaturization of DNA chips to be examined can be achieved because of high freedom of chip design in the present invention. That is, laser beam sources can be disposed in a minimum space except for a driving mechanism, and the laser beam sources and the switching and coupling means 22 can be stably fixed by an apparatus comprising a driving mechanism. Accordingly, unstable operation due to mechanical vibration can drastically be avoided as compared with the air-waveguide system.

The present invention is applicable to other scanning methods. Also, the matching of fluorescent materials used and laser beam sources is important, and the number of laser beam sources may be changed depending on information to be sought.

Figure 6:
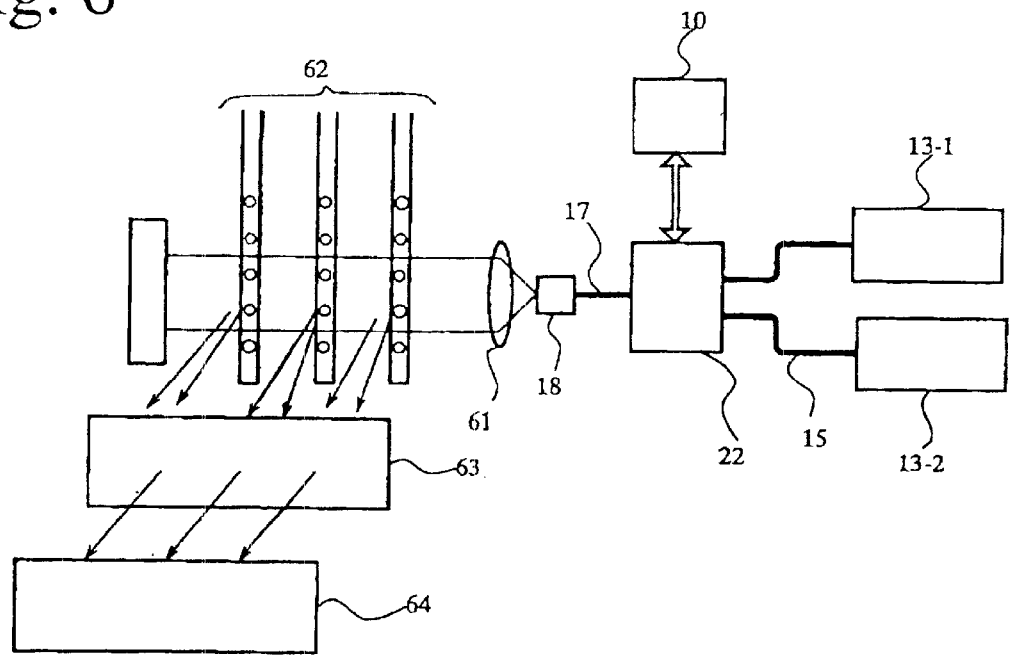
FIG. 6 is a schematic view showing a laser-applied apparatus comprising a laser apparatus coupled with a DNA sequencer according to a still further embodiment of the present invention.

FIG. 6 shows the laser apparatus of the present invention applied to a DNA sequencer. The DNA sequencer comprises, as two laser beam sources having different wavelengths, a small green SHG laser beam source 13-1 having a wavelength of 532 nm, and a semiconductor laser beam source 13-2 having a wavelength of 635 nm, which are connected to optical fibers 15, which are then connected to a DNA chip examination apparatus via a switching and coupling means 22 according to a system as shown in FIG. 2. The laser beam selected by the switching and coupling means 22 irradiates a plurality of capillaries 62. Because DNA fractions are labeled with two fluorescent materials having different wavelengths, fluorescent lights having different wavelengths are simultaneously emitted from the DNA fractions passing through the capillaries 62 by irradiation of laser beams. The fluorescent light scattered in different directions from that of the laser beam is separated by a notch filter 63 and detected by a light detector 64 as a fluorescent light signal together with information of the position of the capillary and time, to conduct the analysis of base sequence. In the present invention, a plurality of information can be obtained by switching the above two laser beam sources 13-1, 13-2 having different wavelengths at a high speed within a time period in which each DNA fraction passes through the laser beam path width. Incidentally, the controller 10 in FIG. 6 has the same function as in the above example.

In this example, too, high reliability of data and high freedom of design for miniaturization are obtained as in FIG. 4. Also, because all light paths to a collimating optical system 61 are constituted by optical fibers, laser beams can easily be switched in response to the variations of fluorescent labels. As is clear from the above, this example provides the same effects as in the above examples.

Figure 7:
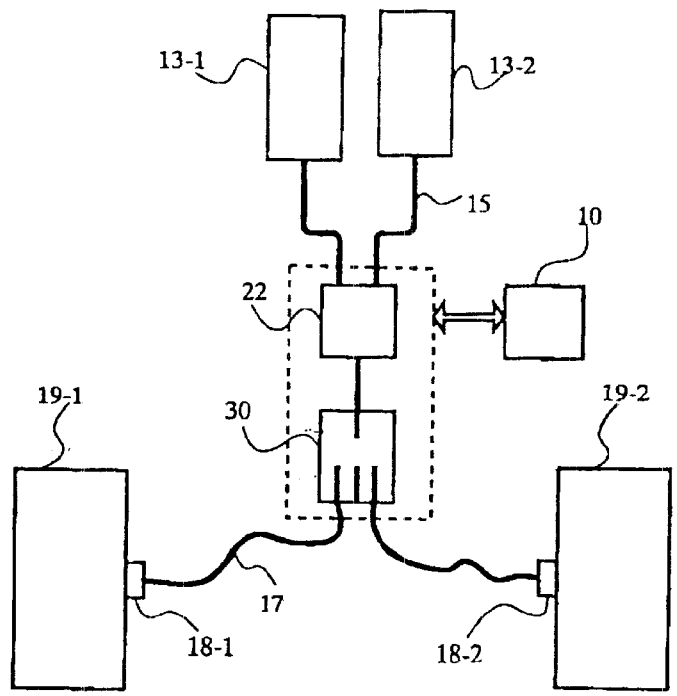
FIG. 7 is a schematic view showing a laser apparatus coupled with a plurality of laser-applied apparatuses according to a still further embodiment of the present invention.
Figure 8:
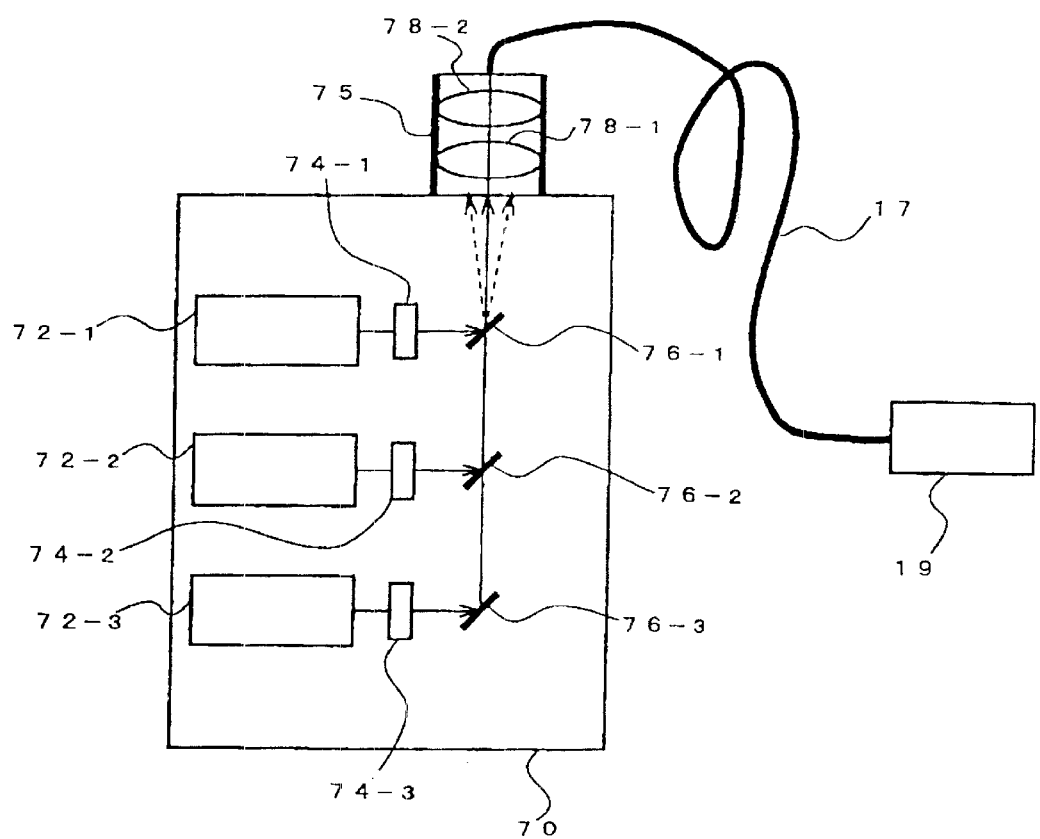
FIG. 8 is a schematic view showing a conventional laser apparatus.

FIG. 7 shows a constitution in which the output laser beams of the laser apparatus of the present invention are sent to both a DNA chip examination apparatus and a DNA sequencer in parallel. The operation principle of the DNA chip examination apparatus and the DNA sequencer has already been explained above referring to FIGS. 5 and 6. It is seldom that the laser-applied apparatuses 19-1, 19-2 in FIG. 7 are operated simultaneously 24 hours a day, and they usually are used alone. Rise time of the laser beam sources until they reach stable operation conditions is usually several minutes to several tens of minutes. Further, the troubles of the laser beam sources tend to take place at the time of repeated ON/OFF operations or after a long period of stop, rather than during the continuous operation. The constitution shown in FIG. 7 solves such problems. Specifically, a dividing switch 30 is disposed downstream of the switching and coupling means 22 shown in FIG. 2, and two outputs supplied from the dividing switch 30 are supplied to laser beam-introducing means 18-1, 18-2 of each apparatus. The dividing switch 30 comprises, in addition to the two outputs terminals, an OFF switch function that keeps laser beams from being supplied to both apparatuses when they are not operated. As compared with the conventional apparatuses, the apparatus of this example can reduce the laser beam sources to half, while reducing the rise time due to decrease in the number of ON/OFF operations, which may cause troubles. Further, this apparatus makes measurement operation easy with reduced risk during the operation, thereby providing an effective laser station.

As described above in detail, the present invention has solved the problems of troublesome and dangerous operations inherent in the conventional laser apparatuses, by providing highly reliable and easy-to-operate, miniaturized laser apparatus and laser-applied apparatus.

What is claimed is:

1. A laser apparatus to supply, selectively, a plurality of laser beams of 30 nm or more in wavelength difference to a measuring apparatus, comprising: optical fibers through which said laser beams pass, and a switching and coupling unit connected to said optical fibers to select at least one laser beam from a plurality of laser beams, each of said optical fibers connected to a plurality of laser beam sources to emit said laser beams having different wavelengths being connected directly to said switching and coupling unit without mixing a plurality of wavelengths of said plurality of laser beams.

2. The laser apparatus according to claim 1, wherein said switching and coupling unit has at least a function to turn off said laser beams.

3. The laser apparatus according to claim 1, wherein said switching and coupling unit comprises a plurality of switching and coupling units that are connected in series or in parallel.

4. The laser apparatus according to claim 3, wherein each of said switching and coupling units comprises input terminals connected to said optical fibers together with at least one NULL terminal not connected to said optical fibers, said terminals being arranged in parallel at an equal interval, wherein an output optical fiber is slidable transversely relative to the parallel arrangement of said terminals, such that said output optical fiber is connected to one of said terminals.

5. The laser apparatus according to claim 1, wherein said switching and coupling unit has a function to position each of said optical fibers to be connected thereto.

6. A laser apparatus to supply, selectively, a plurality of laser beams of 30 nm or more in wavelength difference to a measuring apparatus, comprising: a plurality of laser beam sources to emit laser beams having different wavelengths; a plurality of input optical fibers each connected to said laser beam source, through which said laser beams pass; at least one switching and coupling unit having a plurality of inputs connected to said input optical fibers and at least one output to select at least one laser beam from a plurality of said laser beams; at least one output optical fiber connected to said output of said switching and coupling unit; and a measuring apparatus connected to said output optical fiber, each of said input optical fibers being connected directly to said at least one switching and coupling unit without mixing a plurality of wavelengths of said plurality of laser beams.

7. A laser apparatus to supply, selectively, a plurality of laser beams of 30 nm or more in wavelength difference to a measuring apparatus, comprising: a plurality of laser beam sources to emit laser beams having different wavelengths; a plurality of input optical fibers each connected to said laser beam source, through which said laser beams pass; at least one switching and coupling unit having a plurality of inputs connected to said input optical fibers and at least one output to select at least one laser beam from a plurality of said laser beams; at least one output optical fiber connected to said output of said switching and coupling unit; and a measuring apparatus connected to said output optical fiber, wherein said switching and coupling unit comprises input terminals connected to said input optical fibers together with at least one NULL terminal not connected to said input optical fiber, said terminals being arranged in parallel at an equal interval, wherein said output optical fiber is slidable transversely relative to the parallel arrangement of said terminals, such that said output optical fiber is connected to one of said terminals.

8. A laser-applied apparatus comprising: a fluorescent microscope, and a laser apparatus to supply, selectively, a plurality of laser beams of 30 nm or more in wavelength difference to said fluorescent microscope, said laser apparatus comprising optical fibers through which said laser beams pass, and a switching and coupling unit connected to said optical fibers to select at least one laser beam from a plurality of laser beams.

9. A laser-applied apparatus comprising: a fluorescent microscope, and a laser apparatus to supply, selectively, a plurality of laser beams of 30 nm or more in wavelength difference to said fluorescent microscope, said laser apparatus comprising a plurality of laser beam sources to emit laser beams having different wavelengths; a plurality of input optical fibers each connected to said laser beam source, through which said laser beams pass; at least one switching and coupling unit having a plurality of inputs connected to said input optical fibers and at least one output to select at least one laser beam from a plurality of said laser beams; and at least one output optical fiber connected between said output of said at least one switching and coupling unit and said fluorescent microscope.

10. A laser-applied apparatus comprising: a DNA sequencer, and a laser apparatus to supply, selectively, a plurality of laser beams of 30 nm or more in wavelength difference to said DNA sequencer, said laser apparatus comprising optical fibers through which said laser beams pass, and a switching and coupling unit connected to said optical fibers to select at least one laser beam from a plurality of laser beams.

11. A laser-applied apparatus comprising: a DNA sequencer, and a laser apparatus to supply, selectively, a plurality of laser beams of 30 nm or more in wavelength difference to said DNA sequencer, said laser apparatus comprising a plurality of laser beam sources to emit laser beams having different wavelengths; a plurality of input optical fibers each connected to said laser beam source, through which said laser beams pass; at least one switching and coupling unit having a plurality of inputs connected to said input optical fibers and at least one output to select at least one laser beam from a plurality of said laser beams; and at least one output optical fiber connected between said output of said at least one switching and coupling unit and said DNA sequencer.

12. A laser-applied apparatus comprising: an examination apparatus, and a laser apparatus to supply, selectively, a plurality of laser beams of 30 nm or more in wavelength difference to said examination apparatus, said laser apparatus comprising optical fibers through which said laser beams pass, and a switching and coupling unit connected to said optical fibers to select at least one laser beam from a plurality of laser beams.

13. The laser-applied apparatus according to claim 12, wherein said examination apparatus is a DNA chip examination apparatus, a protein examination apparatus or a DNA probe array examination apparatus.

14. A laser-applied apparatus comprising: an examination apparatus, and a laser apparatus to supply, selectively, a plurality of laser beams of 30 nm or more in wavelength difference to said examination apparatus, said laser apparatus comprising a plurality of laser beam sources to emit laser beams having different wavelengths; a plurality of input optical fibers each connected to said laser beam source, through which said laser beams pass; at least one switching and coupling unit having a plurality of inputs connected to said input optical fibers and at least one output to select at least one laser beam from a plurality of said laser beams; and at least one output optical fiber connected between said output of said switching and coupling unit and said examination apparatus, each of said input optical fibers being connected directly to said switching and coupling unit without mixing a plurality of wavelengths of said plurality of laser beams.

15. The laser-applied apparatus according to claim 14, wherein said examination apparatus is a DNA chip examination apparatus, a protein examination apparatus or a DNA probe array examination apparatus.

* * * * *